US00PP21303P3

(12) United States Plant Patent
Membrey

(10) Patent No.: US PP21,303 P3
(45) Date of Patent: Sep. 21, 2010

(54) ***ARENARIA* PLANT NAMED 'SAPARE'**

(50) Latin Name: *Arenaria monatana*
Varietal Denomination: Sapare

(75) Inventor: Stephen Membrey, Frankston (AU)

(73) Assignees: Stegaydan Pty Ltd, Frankston (AU); Southern Advanced Plants Pty Ltd, Frankston (AU)

( * ) Notice: Subject to any disclaimer, the term of this patent is extended or adjusted under 35 U.S.C. 154(b) by 0 days.

(21) Appl. No.: 12/315,125

(22) Filed: Nov. 29, 2008

(65) Prior Publication Data

US 2010/0146676 P1 Jun. 10, 2010

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner*—Kent L Bell
(74) *Attorney, Agent, or Firm*—Mark P. Bourgeois

(57) ABSTRACT

A new cultivar of *Arenaria* plant named 'Sapare' that is characterized by short height, a compact habit and white flowers.

1 Drawing Sheet

Botanical classification: *Arenaria monatana.*
Variety denomination: 'Sapare'.

BACKGROUND OF THE INVENTION

The present invention relates to a new and distinct cultivar of *Arenaria* plant botanically known as *Arenaria* monatana and hereinafter referred to by the cultivar name 'Sapare'.

'Sapare' was discovered as a single plant in an outdoor seed bed of unidentified *Arenaria monatana* plants in a cultivated area of Dromana, Victoria, Australia in 2004.

Asexual reproduction of the new cultivar 'Sapare' first occurred by terminal cuttings in 2004 in Dromana, Victoria, Australia.

Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Arenaria* cultivar 'Sapare'. These traits in combination distinguish 'Sapare' as a new and distinct cultivar apart from other existing known varieties of *Arenaria.*

1. *Arenaria* 'Sapare' exhibits a short plant height and a compact habit.
2. *Arenaria* 'Sapare' exhibits white flowers.

The closest comparison cultivar is *Arenaria* 'Avalanche' (not patented). 'Sapare' is distinguishable from 'Avalanche' by the following characteristics:

1. 'Sapare' grows to one-half the height of 'Avalanche'.

BRIEF DESCRIPTION OF THE DRAWING

The accompanying photograph illustrates the distinguishing traits of *Arenaria* 'Sapare'. The plant in the photograph shows an overall view of a 26 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Arenaria* cultivar named 'Sapare'. Data was collected in Dromana, Victoria, Australia from 26 week old outdoor grown plants in 12 cm. diameter containers. The time of year was Winter in the Southern Hemisphere. Color determinations are in accordance with The Royal Horticultural Society Colour Chart 2007 edition, except where general color terms of ordinary dictionary significance are used. The growing requirements are similar to the species. 'Sapare' has not been tested under all possible conditions and phenotypic differences may be observed with variations in environmental, climatic, and cultural conditions, however, without any variance in genotype.

Botanical classification: *Arenaria monatana* 'Sapare'.
Use: Ornamental Perennial.
Parentage: Unknown.
Vigor: Moderate.
Growth habit: Ground hugging.
Plant shape: Rounded.
Suitable container size: 12 cm.
Height: 30 cm. in height.
Width: 60 cm. in width.
Low Temperature Tolerance: 2° Centigrade.
High Temperature Tolerance: 30° Centigrade.
Propagation: Terminal cuttings.
Root system: Fibrous.
Stem:
- *Branching habit.*—Upright, freely branching.
- *Average number of lateral branches.*—56.
- *Lateral branch diameter.*—Average 4 mm. in diameter.
- *Lateral branch length.*—Average 25 cm. in length.
- *Stem color.*—143C.
- *Internode length.*—Approximately 1 cm. between nodes.

Foliage:
- *Texture.*—Smooth.
- *Leaf arrangement.*—Opposite.
- *Compound or single.*—Single.
- *Leaf shape.*—Ovate.
- *Leaf dimensions.*—2 cm. in length and 1 cm. in width.

*Leaf base.*—Rounded.
*Leaf apex.*—Rounded.
*Leaf margin.*—Entire.
*Leaf attachment.*—Sessile.
*Leaf color* (*lower surface*).—143C.
*Leaf color* (*upper surface*).—143C.

Flower:
*Inflorescence type.*—Cyme.
*Quantity of flowers per inflorescence.*—Average 5.
*Quantity of flowers and buds per plant.*—160.
*Flowering habit.*—Continuous.
*Flowering season.*—November to February in the Southern Hemisphere.
*Flower bud length.*—4 mm. in length.
*Flower bud diameter.*—3 mm. in diameter.
*Flower bud shape.*—Ovate.
*Bud color.*—N155A.
*Fragrance.*—None.
*Flower shape.*—Rotate.
*Lastingness of flowers.*—approximately 2 weeks.
*Flower dimensions.*—Average 4.0 cm. in diameter and 1.0 cm. in height.
*Petal texture.*—Velvety, soft.
*Number of petals.*—5.
*Fused or unfused.*—Unfused.
*Petal shape.*—Orbicular.
*Petal margin.*—Entire.
*Petal base.*—Rounded.
*Petal apex.*—Obtuse.
*Petal length.*—1.8 cm.
*Petal width.*—1.8 cm.
*Petal color* (*upper and lower surfaces*).—N155A.
*Self-cleaning or persistent.*—Self-cleaning.
*Number of sepals.*—4.
*Sepal margin.*—Entire.
*Sepal apex.*—Acute.
*Sepal base.*—Broad cuneate.
*Sepal dimensions.*—3 mm. in length and 1.5 mm. in width.
*Sepal color* (*upper side*).—143C.
*Sepal color* (*under side*).—143C.
*Peduncle dimensions.*—4 cm. in length and 3 mm. in diameter.
*Peduncle color.*—143C.
*Pedicel dimensions.*—3 mm. in length and 0.5 mm. in diameter.
*Pedicel color.*—143C.

Reproduction organs:
*Stamen number.*—Average 12.
*Anther shape.*—Oval.
*Anther dimensions.*—0.5 mm. in length, filament 6 mm. in length.
*Anther color.*—N157A.
*Filament color.*—N158B.
*Amount of pollen.*—Low.
*Pollen color.*—5D.
*Pistil number.*—3.
*Pistil length.*—3 mm.
*Stigma shape.*—Club shaped.
*Stigma color.*—145C.

Disease and pest resistance: Disease and pest resistance has not been observed.

I claim:

1. A new and distinct variety of *Arenaria* plant named 'Sapare' as described and illustrated.

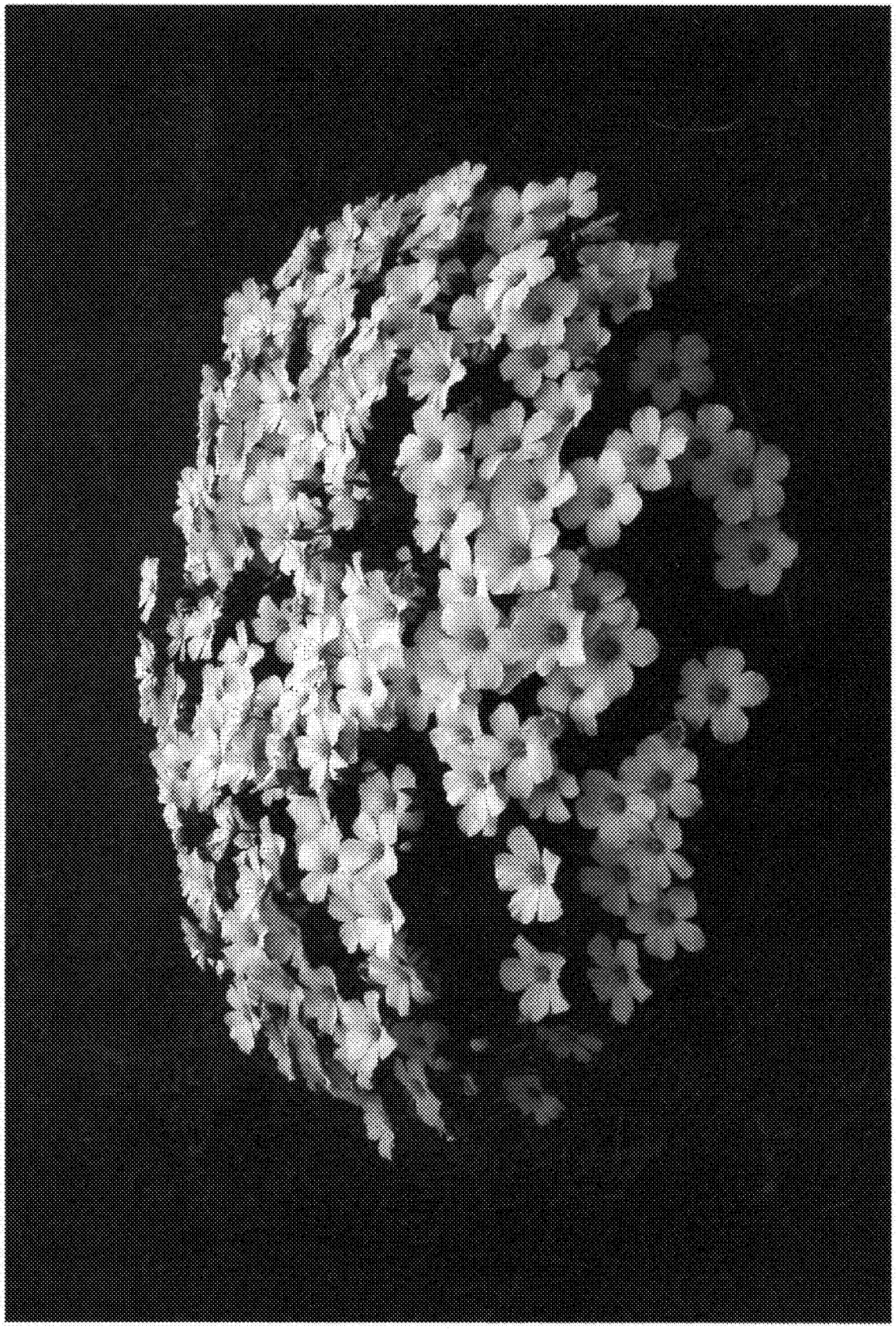

* * * * *